United States Patent [19]

Holtkamp

[11] Plant 5,129

[45] Nov. 1, 1983

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 300,518

[22] Filed: Sep. 9, 1981

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new cultivar of African violet known by the cultivar name Nebraska and having attractive semi-double to double orchid purple blossoms with partly white edges, with the edges being heavily frilled. There are 7–9 slightly tilted flower stems, each of which carries eleven or more flowers, thereby presenting a relatively loose flower head. The petals are long lasting and non-dropping.

1 Drawing Figure

1

The present invention comprises a new and distinct cultivar of African violet plant, botanically known as *Saintpaulia ionantha,* and hereinafter referred to by the cultivar name Nebraska.

The new cultivar was referred to during the breeding and selection process by the designation d 181/3, and is a product of a planned breeding program. The basic objective of the breeding program was to create a new African violet cultivar having semi-double shape, frilled flower edges, and purple flower colors.

The new cultivar was originated from a cross made in a controlled breeding program in Isselburg, West Germany. The female, or seed parent was a cultivar designated b 16/40 bordeaux frilled. The male, or pollen parent was a cultivar designated b 265/4 red star.

The new cultivar Nebraska was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Nebraska has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Nebraska, which in combination distinguish this African violet as a new and distinct cultivar:

(1) Attractive semi-double to double orchid purple blossom with partly white edges.

(2) Heavily frilled.

(3) Seven to nine slightly tilted flower stems.

(4) Eleven or more flowers per stem.

(5) Uniform in growth.

(6) Saleable plant with loose flower head (corolla) within 10 weeks after potting.

2

(7) Long lasting and non-dropping petals.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat, cv. Nebraska.

Parentage:

*Male parent.*—b 265/4 red star.

*Female parent.*—b 16/40 bordeaux frilled.

Propagation: The new cultivar holds its distinguishing characteristics through successive propagations by leaf cuttings and by division of shoots.

Plant: From 6 cm. to 8 cm. tall when grown in pots, and approximately 25 cm. in diameter when fully grown.

*Leaves.*—General Form: Oval. Diameter: Up to 55 mm. Texture: Leathered and hairy. Aspect: Slightly shiny. Veins: Upperside visible; underside well-pronounced. Color (upperside): Parsley green 00962. Color (underside): Sage green 000861/3. Petiole: Young petiole brownish, very hairy; old petiole light green and hairy.

Flowers:

*Buds.*—Ball-shaped; 6–8 mm. just before opening; 11 or more per stem.

*Sepals.*—Color: Brownish green. Calyx: Flat, funneled. Aspect: Spear-shaped. Peduncle: Short upright brownish; very hairy.

*Individual flowers.*—Size: Up to 35 mm. Color: Upperside: Beetroot purple 830/3 w. partly-totally creamy white edges. Underside: Cyclamen purple. Variation: When grown under cooler conditions, the flower color is somewhat more intense. Borne: Flower stem carries up to 11 flowers on short strong peduncle; semi-double. Shape: Conventional; 2 small and 3 large petals; up to 9 petals on occasion; wavy-frilled. Flowering time: First flowers appear 6–7 weeks after potting; after 8–10 weeks full flowering saleable plant.

Reproductive organs:

*Stamens.*—Up to 4 anthers, composed of 2 cells, with seed capsule.

*Anthers.*—Dresden yellow 64.

*Filaments.*—3 mm. long; Dresden yellow 64/3.

*Styles.*—8 mm. purplish; base of ovary Dresden yellow 64/3, hairy.

*Pollen color.*—HCC Dresden yellow 64/3.

Roots: White when young and active; greenish brown when older; normally developed.

Disease resistance: Good as experienced to date.

General observations: Nebraska is a normal growing variety with attractive purple frilled blossom with partly to totally white edges; the flower stems are slightly tilted yet sturdy and carry up to 11 or more individual semi-double flowers that are long-lasting and non-dropping; older mature flowers change into a paler purple.

I claim:

1. A new and distinct cultivar of African violet known by the cultivar name Nebraska, and particularly characterized as to uniqueness by the combined features of semi-double to double orchid purple blossoms with heavily frilled and partly to totally white edges; 7–9 slightly tilted flower stems, each of which contains eleven or more flowers; uniform growth; saleability with loose corolla within 10 weeks after potting, and its long lasting and non-dropping petals.

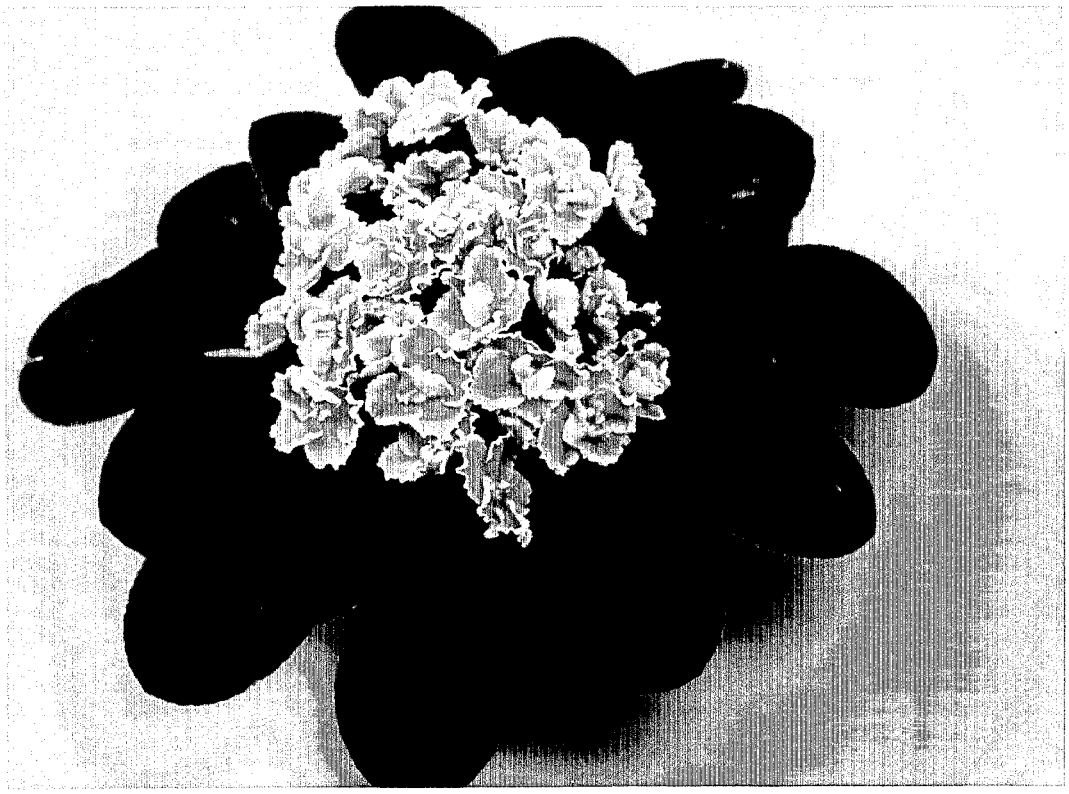

* * * * *